(12) United States Patent
Novak, III et al.

(10) Patent No.: US 11,372,153 B2
(45) Date of Patent: Jun. 28, 2022

(54) CARTRIDGE ORIENTATION FOR SELECTION OF A CONTROL FUNCTION IN A VAPORIZATION SYSTEM

(71) Applicant: RAI Strategic Holdings, Inc., Winston-Salem, NC (US)

(72) Inventors: Charles Jacob Novak, III, Winston-Salem, NC (US); Sean A. Daugherty, Yadkinville, NC (US); Michael Ryan Galloway, Winston-Salem, NC (US); Jason L. Wood, Lexington, NC (US); Matthew Joel Nettenstrom, Bartlett, IL (US); Raymond Charles Henry, Jr., Cary, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 431 days.

(21) Appl. No.: 16/662,410

(22) Filed: Oct. 24, 2019

(65) Prior Publication Data

US 2020/0154786 A1 May 21, 2020

Related U.S. Application Data

(60) Provisional application No. 62/769,296, filed on Nov. 19, 2018.

(51) Int. Cl.
*F21V 8/00* (2006.01)
*A61M 11/04* (2006.01)
(Continued)

(52) U.S. Cl.
CPC .......... *G02B 6/009* (2013.01); *A61M 11/041* (2013.01); *A61M 11/042* (2014.02);
(Continued)

(58) Field of Classification Search
CPC .............. A61M 11/042; A61M 11/041; A61M 2205/3341; A61M 2205/3576;
(Continued)

(56) References Cited

U.S. PATENT DOCUMENTS 2,057,353 A 10/1936 Whittemore, Jr.
2,104,266 A 1/1938 McCormick
(Continued)

FOREIGN PATENT DOCUMENTS

CN 1541577 11/2004
CN 2719043 8/2005
(Continued)

*Primary Examiner* — Harshad G Patel
(74) *Attorney, Agent, or Firm* — Womble Bond Dickinson (US) LLP

(57) ABSTRACT

The present disclosure relates to aerosol delivery devices comprising a power unit and a cartridge that is configured for engagement with the power unit. In particular, the cartridge can be configured for rotation about a longitudinal axis thereof so as to be insertable into a chamber of the power unit in a plurality of different orientations. Further, the aerosol delivery device can include processing circuitry that can be configured for detection of the cartridge orientation and execution of a control function assigned to the respective orientation.

15 Claims, 7 Drawing Sheets

(51) Int. Cl.
*H02J 7/00* (2006.01)
*F21V 23/00* (2015.01)
*G05B 19/042* (2006.01)
*F21Y 115/10* (2016.01)

(52) U.S. Cl.
CPC .......... *F21V 23/005* (2013.01); *G02B 6/0083* (2013.01); *G05B 19/042* (2013.01); *H02J 7/00* (2013.01); *H02J 7/007* (2013.01); *H02J 7/0063* (2013.01); *A61M 2205/3331* (2013.01); *A61M 2205/3576* (2013.01); *A61M 2205/50* (2013.01); *A61M 2205/587* (2013.01); *F21Y 2115/10* (2016.08); *G05B 2219/2639* (2013.01)

(58) Field of Classification Search
CPC .......... A61M 2205/35; A61M 2205/50; A61M 2205/587; F21V 23/005; F21V 2115/10; G02B 6/009; G02B 6/0083; G02B 19/042; G02B 2219/2639; H02J 7/00; H02J 7/007; H02J 7/0063
USPC ........................................................ 131/329
See application file for complete search history.

(56) References Cited

U.S. PATENT DOCUMENTS

| | | | |
|---|---|---|---|
| 3,200,819 A | 8/1965 | Gilbert | |
| 4,922,901 A | 5/1990 | Brooks et al. | |
| 5,060,671 A | 10/1991 | Counts et al. | |
| 5,093,894 A | 3/1992 | Deevi et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2* | 11/2010 | Hon | H05B 1/0291 128/200.14 |
| 8,314,591 B2 | 11/2012 | Terry et al. | |
| 8,365,742 B2 | 2/2013 | Hon | |
| 8,499,766 B1 | 8/2013 | Newton | |
| 8,528,569 B1 | 9/2013 | Newton | |
| 8,833,364 B2 | 9/2014 | Buchberger | |
| 9,220,302 B2* | 12/2015 | DePiano | A24F 40/70 |
| 9,220,304 B2 | 12/2015 | Greim | |
| 9,462,831 B2 | 10/2016 | Liu | |
| 9,507,466 B2* | 11/2016 | Moore | G06F 21/83 |
| 9,597,466 B2* | 3/2017 | Henry, Jr | A61M 11/042 |
| 9,609,893 B2* | 4/2017 | Novak, III | H05B 3/00 |
| 9,877,508 B2 | 1/2018 | Kane | |
| 9,934,741 B1* | 4/2018 | Pan | G09G 3/3648 |
| 10,004,259 B2* | 6/2018 | Sebastian | A24F 40/30 |
| 10,015,990 B2 | 7/2018 | Mironov | |
| 10,028,537 B1 | 7/2018 | Hawes et al. | |
| 10,058,125 B2 | 8/2018 | Worm et al. | |
| 10,080,851 B2 | 9/2018 | Davidson et al. | |
| 10,085,481 B2* | 10/2018 | Verleur | H02J 7/0042 |
| 10,092,037 B2 | 10/2018 | Tucker et al. | |
| 10,104,913 B2 | 10/2018 | Lau et al. | |
| 10,117,463 B2 | 11/2018 | Thomas | |
| 10,117,467 B2 | 11/2018 | Hawes et al. | |
| 10,876,879 B2* | 12/2020 | Colotte | A24F 40/51 |
| 2005/0016550 A1* | 1/2005 | Katase | A24F 40/50 131/194 |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0151717 A1 | 6/2009 | Bowen et al. | |
| 2009/0188490 A1 | 7/2009 | Hon | |
| 2009/0272379 A1 | 11/2009 | Thorens et al. | |
| 2009/0320863 A1 | 12/2009 | Fernando et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2013/0037041 A1 | 2/2013 | Worm et al. | |
| 2013/0042865 A1 | 2/2013 | Monsees et al. | |
| 2013/0306084 A1 | 11/2013 | Flick | |
| 2013/0319435 A1 | 12/2013 | Flick | |
| 2014/0000638 A1 | 1/2014 | Sebastian et al. | |
| 2014/0096781 A1 | 4/2014 | Sears et al. | |
| 2014/0096782 A1 | 4/2014 | Ampolini et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0366898 A1 | 12/2014 | Monsees et al. | |
| 2015/0020832 A1 | 1/2015 | Greim et al. | |
| 2015/0150308 A1 | 6/2015 | Monsees et al. | |
| 2015/0164142 A1 | 6/2015 | Li et al. | |
| 2015/0208729 A1 | 7/2015 | Monsees et al. | |
| 2015/0313287 A1 | 11/2015 | Verleur et al. | |
| 2016/0158782 A1* | 6/2016 | Henry, Jr | F22B 1/284 700/275 |
| 2017/0027226 A1 | 2/2017 | Mironov et al. | |
| 2017/0071256 A1 | 3/2017 | Verleur et al. | |
| 2017/0095005 A1 | 4/2017 | Monsees et al. | |
| 2017/0135404 A1 | 5/2017 | Reevell | |
| 2017/0135405 A1 | 5/2017 | Reevell | |
| 2017/0143042 A1 | 5/2017 | Batista et al. | |
| 2017/0215485 A1 | 8/2017 | Zitzke | |
| 2017/0231281 A1 | 8/2017 | Hatton et al. | |
| 2017/0231282 A1 | 8/2017 | Hatton et al. | |
| 2017/0251724 A1* | 9/2017 | Lamb | G08B 21/18 |
| 2017/0325289 A1 | 11/2017 | Liu | |
| 2017/0340011 A1 | 11/2017 | Batista | |
| 2017/0340012 A1 | 11/2017 | Mironov et al. | |
| 2017/0347711 A1 | 12/2017 | Litten et al. | |
| 2017/0347712 A1 | 12/2017 | Singh | |
| 2018/0000157 A1 | 1/2018 | Batista et al. | |
| 2018/0000160 A1 | 1/2018 | Taschner et al. | |
| 2018/0014575 A1 | 1/2018 | Fursa | |
| 2018/0020731 A1 | 1/2018 | Rasmussen et al. | |
| 2018/0020736 A1 | 1/2018 | Silvestrini | |
| 2018/0035717 A1 | 2/2018 | Batista | |
| 2018/0042306 A1 | 2/2018 | Atkins et al. | |
| 2018/0043114 A1 | 2/2018 | Bowen et al. | |
| 2018/0077967 A1 | 3/2018 | Hatton et al. | |
| 2018/0084831 A1 | 3/2018 | Mironov | |
| 2018/0103685 A1 | 4/2018 | Yener | |
| 2018/0132525 A1* | 5/2018 | Patil | H05B 1/0244 |
| 2018/0140019 A1 | 5/2018 | Guo et al. | |
| 2018/0177230 A1 | 6/2018 | Hawes et al. | |
| 2018/0198297 A1 | 7/2018 | Grzan et al. | |
| 2018/0213850 A1 | 8/2018 | Brinkley et al. | |
| 2018/0242643 A1 | 8/2018 | Silvestrini et al. | |
| 2018/0280637 A1 | 10/2018 | Mayle et al. | |
| 2018/0295888 A1 | 10/2018 | Newcomb et al. | |
| 2018/0296777 A1 | 10/2018 | Terry et al. | |
| 2019/0387797 A1 | 12/2019 | Christensen et al. | |
| 2020/0000146 A1 | 1/2020 | Anderson et al. | |

FOREIGN PATENT DOCUMENTS

| | | |
|---|---|---|
| CN | 201379072 | 1/2010 |
| EP | 1 618 803 | 1/2006 |
| WO | WO 2004/080216 | 9/2004 |
| WO | WO 2005/099494 | 10/2005 |
| WO | WO 2007/131449 | 11/2007 |
| WO | WO 2016/026811 | 2/2016 |
| WO | WO 2016/124717 | 8/2016 |
| WO | WO 2017/051006 | 9/2016 |
| WO | WO 2017/207442 | 5/2017 |
| WO | WO 2018/167166 | 9/2018 |
| WO | WO 2018/202732 | 11/2018 |

* cited by examiner

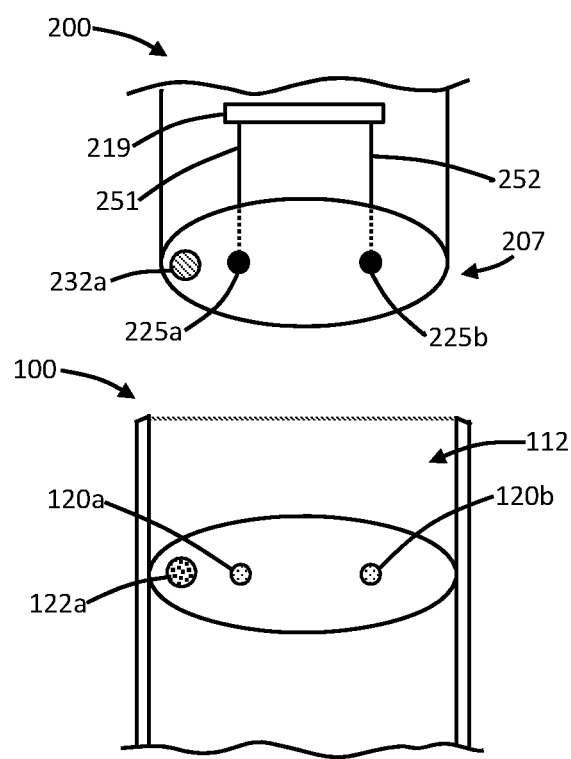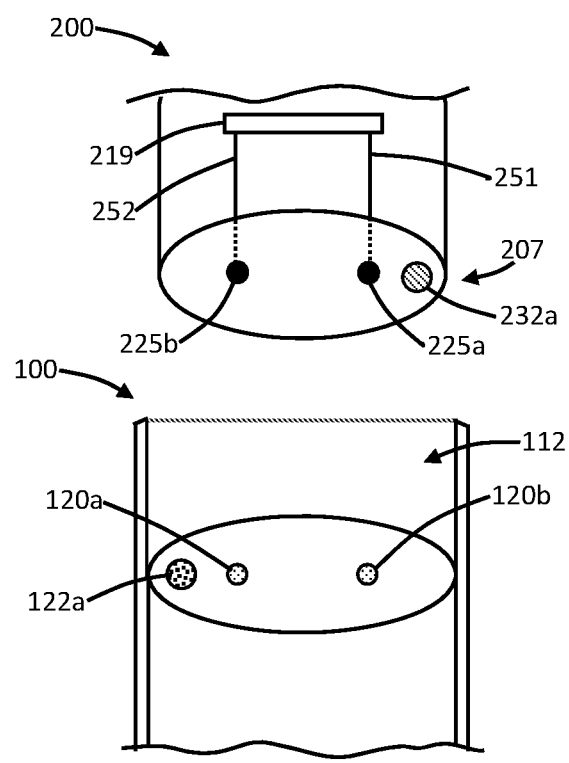

CARTRIDGE ORIENTATION FOR SELECTION OF A CONTROL FUNCTION IN A VAPORIZATION SYSTEM

CROSS-REFERENCE TO RELATED APPLICATIONS

The present application claims priority to U.S. Provisional Patent Application No. 62/769,296, filed Nov. 19, 2018, the disclosure of which is incorporated herein by reference.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference. See also, for example, the various types of smoking articles, aerosol delivery devices, and electrically powered heat generating sources referenced by brand name and commercial source in U.S. Pat. Pub. No. 2015/0216232 to Bless et al., which is incorporated herein by reference.

It would be desirable to provide a vaporization system providing consumers with improved customization ability. It would further be desirable to provide a vaporization system wherein a power level delivered from a power source to a vaporizer can be simply controlled by a user of the device.

SUMMARY OF THE DISCLOSURE

The present disclosure relates to aerosol delivery devices, methods of forming such devices, and elements of such devices. The disclosure particularly can relate to an aerosol delivery system formed of at least one cartridge that is connectable with at least one power unit. The cartridge can be configured for connection with the power unit in at least two different orientations, for example, at least a first orientation and at least a second orientation that is different than the first orientation. The connection between the cartridge and the power unit can be configured such that one or more operational aspects of the aerosol delivery device can be changed depending upon the specific orientation in which the cartridge and the power unit are connected. For example, in the first orientation, a first operational feature may be executed in a first mode and, in the second orientation, a second operational feature may be executed in a second, different mode. In this manner, it is possible to change an operation of the aerosol delivery device by simply changing the connection orientation of the cartridge with the power unit. Beneficially, it is thus possible to eliminate external buttons or the like or limit the number of external buttons or the like that are present on the device.

In some embodiments, the present disclosure may particularly provide an aerosol delivery device comprising: a power unit comprising: a power unit housing having a distal end, a proximal end, and a longitudinal axis extending between the distal end and the proximal end; a power source positioned within the power unit housing; a first interface defined at the proximal end of the power unit housing; and processing circuitry; and a cartridge that is coupleable with the power unit, the cartridge comprising: a cartridge housing having a distal end defining a second interface, a proximal end, and a longitudinal axis extending between the distal end and the proximal end, the cartridge housing being configured for containing an aerosol precursor composition; and a vaporizer positioned within the cartridge housing and operable to vaporize the aerosol precursor composition; wherein the cartridge is configured for rotation about the longitudinal axis of the cartridge housing so as to be coupleable with the power unit in at least a first orientation relative to the power unit and a second, different orientation relative to the power unit; and wherein the processing circuitry of the power unit is configured for detection of whether the cartridge is present in the first orientation or the second, different orientation and executing a control function assigned to the respective orientation. In further embodiments, the aerosol delivery device may be defined in relation to any one or more of the following statements, which may be combined in any number or order.

The power unit further can comprise two electrical connectors positioned at the first interface of the power unit housing, and wherein the cartridge further can comprises two electrical contacts positioned in or on the cartridge housing and configured for making an electrical connection with the two electrical connectors of the power unit when the cartridge is coupled with the power unit, the electrical connection being configured for delivery of electrical current from the power source in the power unit to the vaporizer in the cartridge.

The power unit can comprise a first electrical connector, a second electrical connector, and a third electrical connector.

The aerosol delivery device can be configured such that: the cartridge can comprise a first electrical contact, a second electrical contact, and a third electrical contact; the first electrical contact and the second electrical contact can be in electrical connection with the first electrical connector and the second electrical connector in each of the first orientation and the second, different orientation of the cartridge; and the third electrical contact can be in electrical connection with the third electrical connector in only one of the first orientation and the second, different orientation of the cartridge.

The aerosol delivery device can be configured such that: the cartridge can comprise a first electrical contact and a second electrical contact; the first electrical contact and the second electrical contact can be in electrical connection with the first electrical connector and the second electrical connector in the first orientation of the cartridge; and the first electrical contact and the second electrical contact can be in electrical connection with the second electrical connector and the third electrical connector in the second, different orientation of the cartridge.

The power unit can comprise a first set of two electrical connectors and a second set of two electrical connectors.

The aerosol delivery device can be configured such that: the two electrical contacts of the cartridge can be in electrical connection with the first set of electrical connectors in the first orientation of the cartridge; and the two electrical contacts of the cartridge can be in electrical connection with the second set of electrical connectors in the second, different orientation of the cartridge.

The power unit can comprise a sensing element configured for providing a signal dependent upon whether the cartridge is in the first orientation or the second, different orientation, said signal being detectable by the processing circuitry.

The sensing element can comprise a Hall effect sensor.

The control function can include a power delivery profile.

The processing circuitry can be configured for directing delivery of electrical current from the power source in the power unit to the vaporizer in the cartridge according to a first power delivery profile when the cartridge is in the first orientation and is configured for directing delivery of electrical current from the power source in the power unit to the vaporizer in the cartridge according to a second, different power delivery profile when the cartridge is in the second, different orientation.

The control function can include powering the aerosol delivery device on and off.

The control function can include enabling or disabling a wireless communication capability of the aerosol delivery device.

The control function can include activating a visual effect or a haptic effect of the aerosol delivery device.

The control function can include enabling a set of user settings of the device.

BRIEF DESCRIPTION OF THE FIGURES

Figure 1:
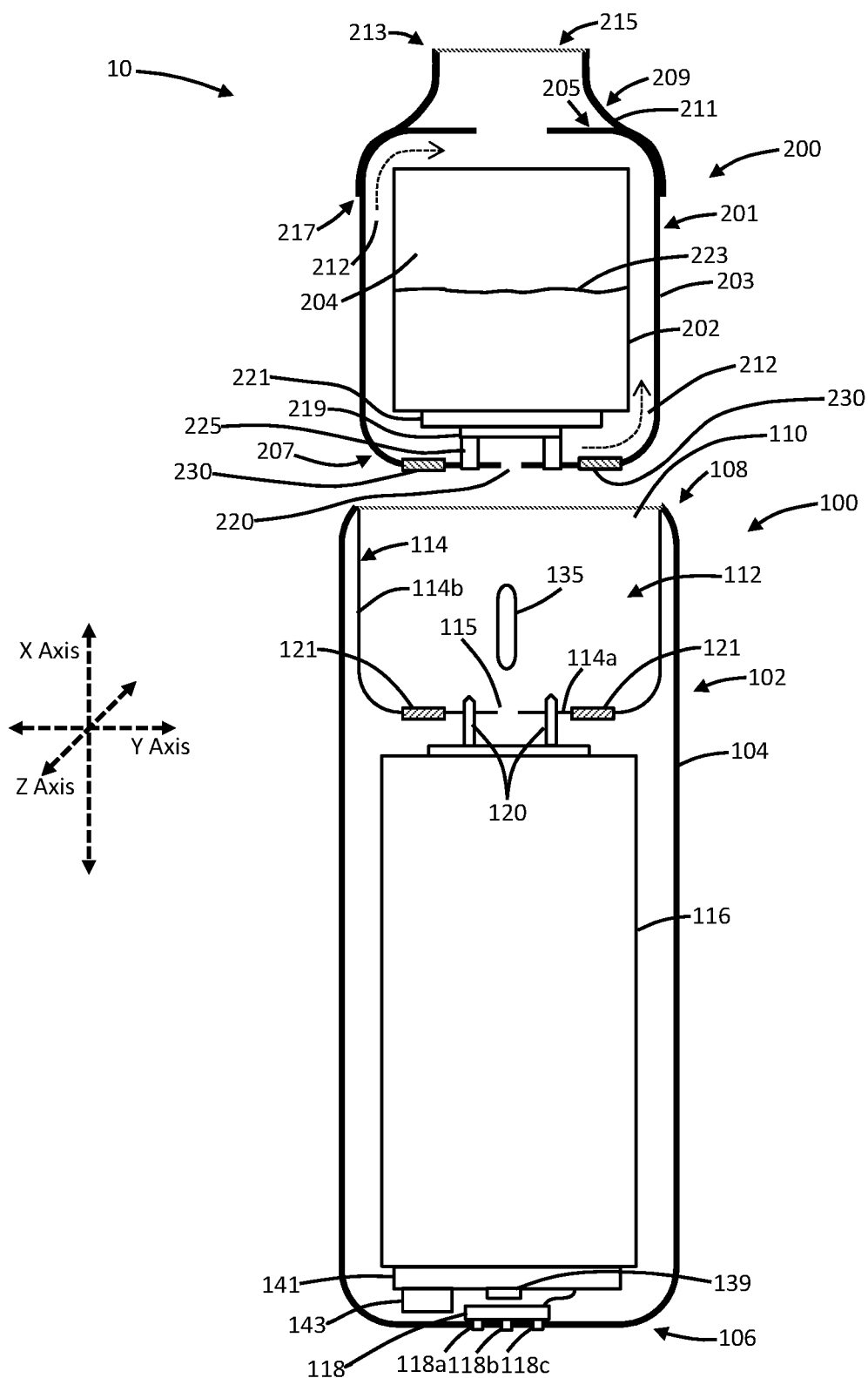
Figure 2A:
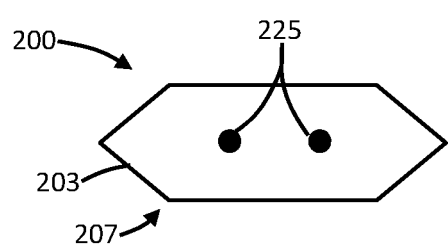
Figure 2B:
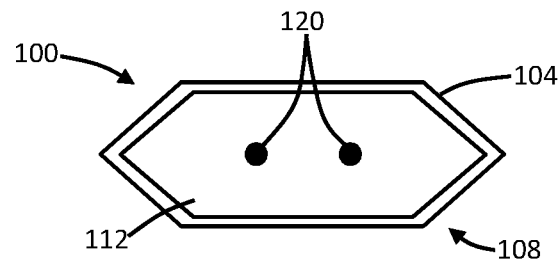
Figure 3A:
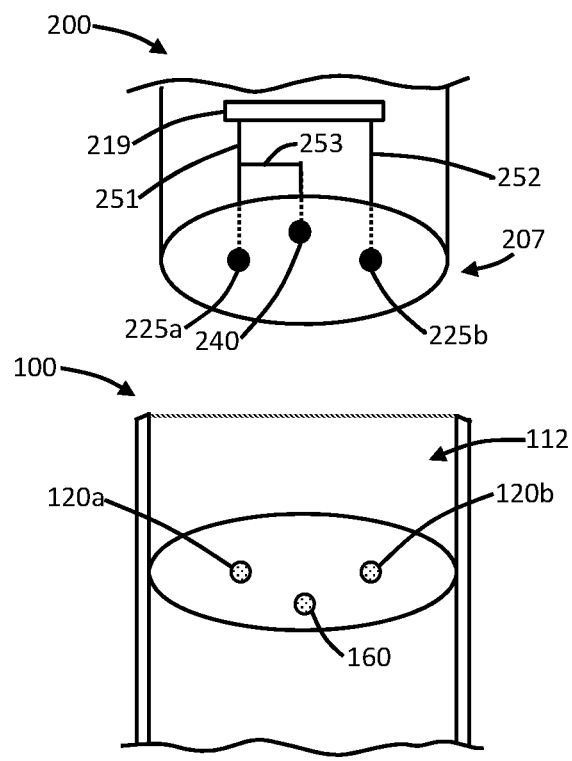
Figure 3B:
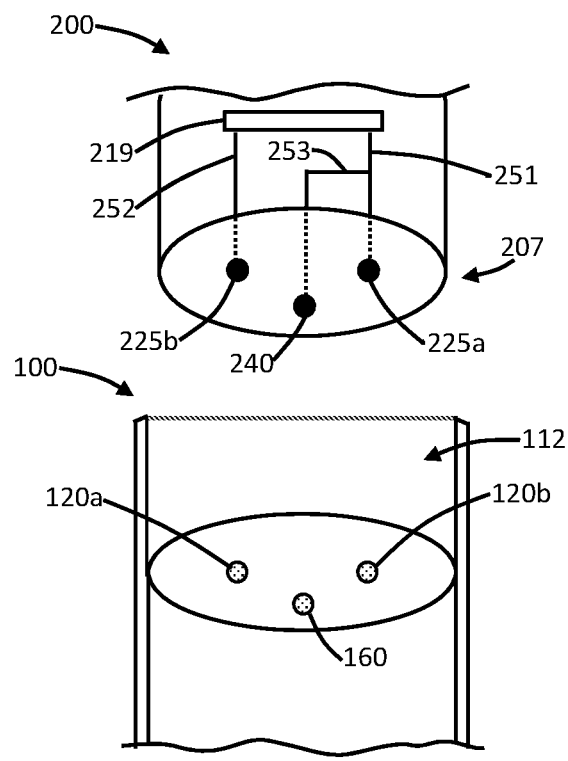
Figure 4A:
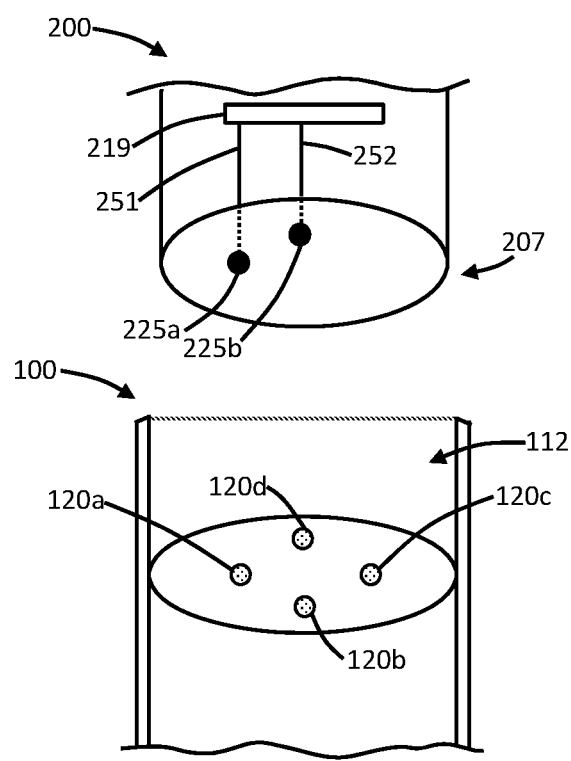
Figure 4B:
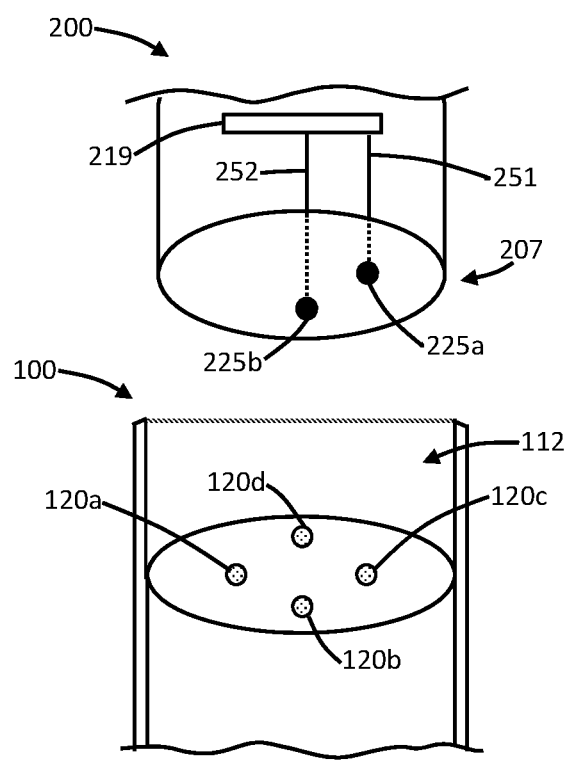
Figure 5A:
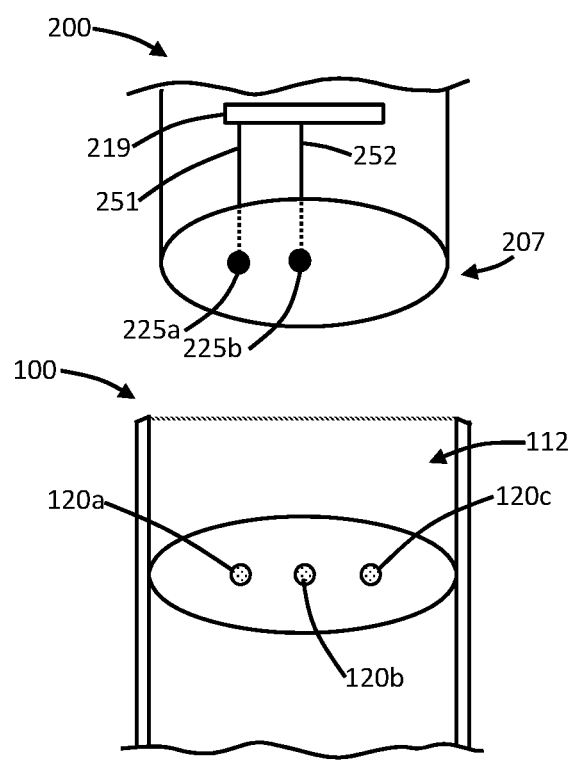
Figure 5B:
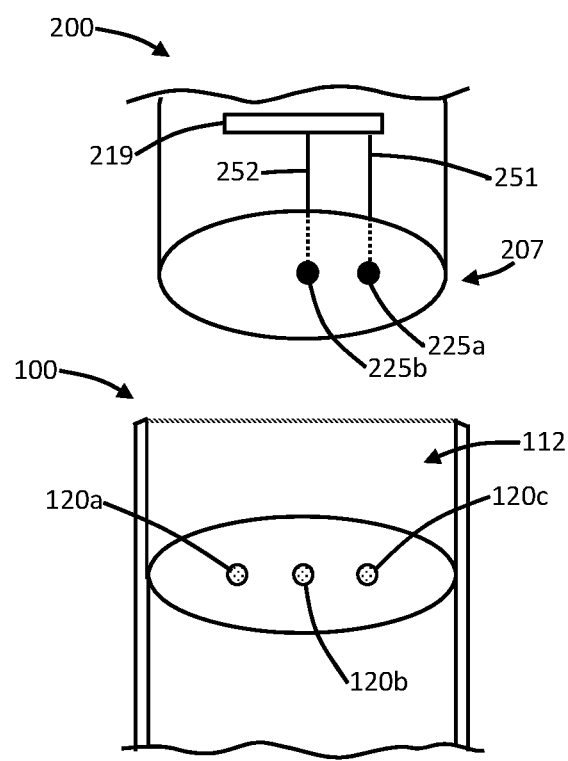
Figure 6A:
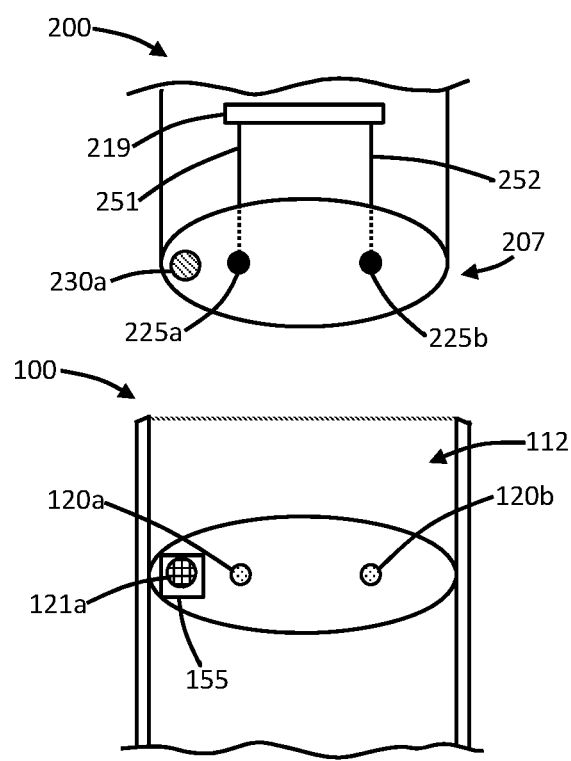
Figure 6B:
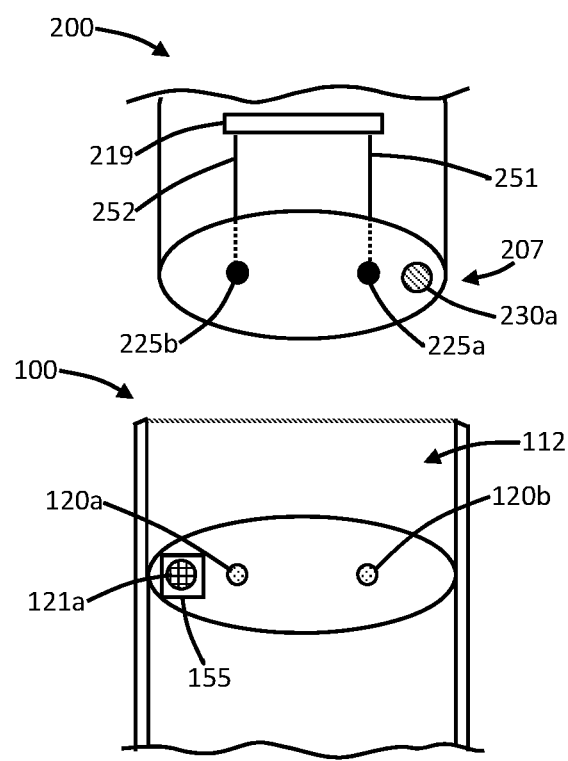
Figure 7:
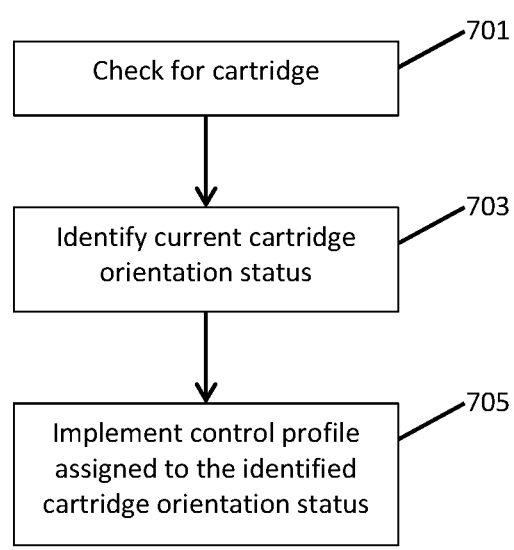

Having thus described the disclosure in the foregoing general terms, reference will now be made to the accompanying drawings, which are not necessarily drawn to scale, and wherein:

FIG. 1 is a partial cross-section of an aerosol delivery device according to example embodiments of the present disclosure;

FIG. 2A is an end view of a cartridge illustrating a configuration of electrical connections according to example embodiments of the present disclosure;

FIG. 2B is an end view of a receptacle of a power unit illustrating a configuration of electrical connections according to example embodiments of the present disclosure;

FIG. 3A is a partial cross-section of a portion of a cartridge and a corresponding receptacle of a power unit illustrating a configuration of electrical connections according to example embodiments of the present disclosure;

FIG. 3B is a partial cross-section of a portion of the cartridge and the corresponding receptacle of the power unit as illustrated in FIG. 3A, wherein the cartridge is rotated 180 degrees about a longitudinal axis thereof relative to the configuration illustrated in FIG. 3A;

FIG. 4A is a partial cross-section of a portion of a cartridge and a corresponding receptacle of a power unit illustrating a configuration of electrical connections according to example embodiments of the present disclosure;

FIG. 4B is a partial cross-section of a portion of the cartridge and the corresponding receptacle of the power unit as illustrated in FIG. 4A, wherein the cartridge is rotated 180 degrees about a longitudinal axis thereof relative to the configuration illustrated in FIG. 4A;

FIG. 5A is a partial cross-section of a portion of a cartridge and a corresponding receptacle of a power unit illustrating a configuration of electrical connections according to example embodiments of the present disclosure;

FIG. 5B is a partial cross-section of a portion of the cartridge and the corresponding receptacle of the power unit as illustrated in FIG. 5A, wherein the cartridge is rotated 180 degrees about a longitudinal axis thereof relative to the configuration illustrated in FIG. 5A;

FIG. 6A is a partial cross-section of a portion of a cartridge and a corresponding receptacle of a power unit illustrating a configuration of electrical connections according to example embodiments of the present disclosure;

FIG. 6B is a partial cross-section of a portion of the cartridge and the corresponding receptacle of the power unit as illustrated in FIG. 6A, wherein the cartridge is rotated 180 degrees about a longitudinal axis thereof relative to the configuration illustrated in FIG. 6A;

FIG. 6C is a partial cross-section of a portion of a cartridge and a corresponding receptacle of a power unit illustrating a configuration of electrical connections according to example embodiments of the present disclosure;

FIG. 6D is a partial cross-section of a portion of the cartridge and the corresponding receptacle of the power unit as illustrated in FIG. 6C, wherein the cartridge is rotated 180 degrees about a longitudinal axis thereof relative to the configuration illustrated in FIG. 6C;

FIG. 7 is a flow chart illustrating a method of selecting a control profile for implementation in an aerosol delivery device according to example embodiments of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems or vaporization systems, said terms being used herein interchangeably. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In various embodiments, components of aerosol delivery systems may be characterized as electronic cigarettes, and those electronic cigarettes may incorporate tobacco and/or components derived from tobacco, and hence deliver tobacco derived components in aerosol form.

Aerosol generating pieces of certain embodiments may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in the background art section of the present disclosure.

In one or more embodiments, the present disclosure relates to an aerosol delivery device including a cartridge and a power unit. The cartridge engages the power unit such that the position of the cartridge relative to the power unit can define a plurality of different orientations. In particular, the cartridge can engage the power unit in two different orientations, at least two different orientations, three different orientations, at least three different orientations, four different orientations, at least four different orientations, or even more different orientations.

An example embodiment of an aerosol delivery device 100 is shown in FIG. 1. As seen therein, the aerosol delivery device 10 comprises a power unit 100 and a cartridge 200. The cartridge 200 is engagable with the power unit 100 to form an operating aerosol delivery device, and the cartridge is removable therefrom.

The power unit can comprise an outer housing 102 that defines a power unit outer wall 104, a power unit distal end 106, and a power unit proximal end 108. The power unit proximal end 108 defines a first interface for coupling of the power unit with a cartridge. The first interface defined at the proximal end may include an opening 110 that provides access to a power unit chamber 112 that is defined by a power unit inner frame 114. While the chamber 112 can provide a desired coupling in some embodiments, the first interface may take on other configurations as described herein that allow for alternative orientations of the connection of the cartridge with the power unit.

In some embodiments, the power unit inner frame 114 may include an aperture 115 that can be configured for transferring pressure differentials therethrough to a sensor 143 positioned within the power unit 100 when air is drawn into the device 10. As illustrated, the sensor 143 is positioned on a printed circuit board (PCB). Configurations of a PCB and a pressure sensor, for example, are described in U.S. Pat. Pub. No. 2015/0245658 to Worm et al., the disclosure of which is incorporated herein by reference. The sensor 143 can be positioned anywhere within the power unit 100 so as to subject to airflow and/or a pressure change that can signal a draw on the device and thus cause the battery 116 to delivery power to the vaporizer 219 in the cartridge 200. Alternatively, in the absence of an airflow sensor, the vaporizer 219 may be activated manually, such as by a push button. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

The power unit 100 further can include a battery 116 positioned within the power unit outer housing 102. Examples of batteries that can be used according to the disclosure are described in U.S. Pat. Pub. No. 2010/0028766 to Peckerar et al., the disclosure of which is incorporated herein by reference. The power unit 100 still further can include an external connection element 118. Preferably, the external connection element 118 is positioned at the distal end 106 of the power unit outer housing 102 and can be formed of a plurality of electrical connectors (118a, 118b, 118c). In one or more embodiments, the power unit 100 may include a light source 139 that may comprise, for example, one or more light emitting diodes (LED) capable of providing one or more colors of lighting. The first light source 139 can be positioned directly on a printed circuit board (PCB) 141, and the PCB can include further control components (e.g., a microcontroller and/or memory components). As illustrated, the sensor 143 and the external connection element 118 are likewise directly attached to the PCB 141 or otherwise electrically connected to the PCB. The power unit further can include electrical connectors 120 (which can be in the form or pins or any other suitable configuration) positioned in the chamber 112 for forming an electrical connection with the cartridge 100 upon insertion of the cartridge into the chamber. As illustrated, the electrical connectors 120 are positioned proximate a bottom portion of the chamber 112 and particularly may extend through a bottom wall 114a of the inner frame 114, which frame defines the boundaries of the chamber 112. One or more mechanical connectors 121 may also be present in the chamber 112, and particularly can be positioned in the inner frame 114, such as in the bottom wall 114a thereof. For example, mechanical connectors 121 can be magnetic elements (e.g., magnets or elements formed of material configured for forming a magnetic connection with a further magnet). Alternatively, the mechanical connectors 121 may be positioned in a side wall 114b of the inner frame 114 and thus may be configure for establishing a friction fit with the cartridge 200.

The power unit outer housing 102 may be formed of any suitable material, such as a metal, plastic, ceramic, glass, or the like. Preferably, the power unit inner frame 114 is formed of the same material as used to form the first device outer housing 102; however, different materials may be used. Although the power unit inner frame 114 is illustrated as being a separate element from the power unit outer housing 102, it is understood that, if desired, the inner frame may be defined by an internal surface of the outer housing and an added bottom plate (i.e., such that the bottom plate corresponds to the illustrated inner frame bottom wall 114a, and the internal surface of the outer housing corresponds to the illustrated inner frame side wall 114b).

A cartridge 100 for use in an aerosol delivery device 10 of the present disclosure can comprise a tank 201 that is defined by an outer tank wall 203 that includes a proximal end 205 and a distal end 207 that defines a second interface for coupling of the cartridge with a power unit. One or more mating connectors 230 can be present at the distal end 207 of the cartridge 200 and can be configured to form a connection with the one or more mechanical connectors 121 present on the power unit 100 (e.g., at the first interface, which may be positioned within the chamber 112). The mating connectors 230, for example, can be magnetic elements (e.g., magnets or elements formed of material configured for forming a magnetic connection with a further magnet). Alternatively, the mating connectors 230 may be present on one or more sides of the outer tank wall 203 and thus may be configured for establishing a friction fit with the chamber 112 of the power unit 100.

The cartridge 200 is configured to contain a liquid composition for vaporization—i.e., an e-liquid or aerosol precursor composition, which may be configured as otherwise described herein. The tank 201 particularly can include an inner wall 202 that defines a reservoir 204 wherein the e-liquid or the like may be retained. An aerosol passage 212 can at least partially surround the reservoir 204 in a longitudinal direction from the distal end 207 to the proximal end 205 of the tank 201. In other embodiments, however, it is understood that the aerosol passage 212 may extend through at least a portion of the reservoir such that the reservoir is configured in an annular space between the aerosol passage and the outer tank wall 203.

The cartridge 200 further can comprise a mouthpiece 209 that is defined by an outer mouthpiece wall 211 that includes a proximal end 213 with an exit portal 215 and a distal end 217 that is engaging the proximal end 205 of the tank 201.

Although the mouthpiece 209 is described as being a separate element from the tank 201, it is understood that the tank wall 203 may extend a greater distance so as to form an integral mouthpiece. As such, the mouthpiece may be attached to the tank, or the mouthpiece may be integrally formed with the tank. The cartridge 200 further can include a vaporizer 219 and a liquid transport element 221 that defines a fluid connection between the vaporizer and a liquid 223 contained within the reservoir 204. The vaporizer 219 and liquid transport element 221 may be configured as separate elements that are fluidly connected or may be configured as a combined element. Moreover, the vaporizer 219 and the liquid transport element 221 may be formed of any construction as otherwise described herein. The cartridge 200 also can include one or more electrical contacts 225 that are configured to electrically connect the vaporizer 219 with the battery 116 in the power unit 100 through contact with the electrical connectors 120 when the cartridge is connected with the power unit.

A liquid transport element 221 can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element). As further discussed herein, some embodiments of the present disclosure can particularly relate to the use of non-fibrous transport elements. As such, fibrous transport elements can be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference. In some embodiments, a liquid transport element can be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference. The porous monolith can form a substantially solid wick.

In one or more embodiments, a vaporizer 219 may specifically include a heater. Various embodiments of materials configured to produce heat when electrical current is applied therethrough may be employed to form the heater. In some embodiments, the heater can be a wire coil. Example materials from which the wire coil may be formed include Kanthal (FeCrAl), Nichrome, Molybdenum disilicide $(MoSi_2)$, molybdenum silicide (MoSi), Molybdenum disilicide doped with Aluminum $(Mo(Si,Al)_2)$, titanium, platinum, silver, palladium, alloys of silver and palladium, graphite and graphite-based materials (e.g., carbon-based foams and yarns). In further embodiments, the heater can be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater in particular may be configured to be substantially flat. Such heaters are described in U.S. Pat. Pub. No. 2016/0345633 to DePiano et al., which is incorporated herein by reference. In further embodiments, a vaporizer 219 may comprise one or more elements adapted to or configured vaporize or aerosolize (or otherwise form a fine, particulate form of) an aerosol precursor liquid without necessarily heating the liquid. For example, a piezo element may be used as a vaporizer in certain embodiments of the present disclosure, and suitable piezo elements are described, for example, in U.S. Pat. Pub. No. 2013/0319404 to Feriani et al. and U.S. Pat. Pub. No. 2019/0014819 to Sur, the disclosures of which are incorporate herein by reference.

The outer tank wall 203 can be configured to be at least partially transparent or translucent so that the liquid 223 contained therein is visible externally. As such, the entire outer tank wall 203 can be transparent or translucent. Alternatively, only a single side of the outer tank wall 203 can be transparent or translucent while the remaining portions of the outer tank wall can be substantially opaque. In further embodiments, the outer tank wall 203 can be colored. The aerosol delivery device 10 can be configured in some embodiments so that at least a portion of the tank 201 is visible when the cartridge 200 is engaged with the power unit 100. Likewise, at least a portion of the inner wall 202 that defines the reservoir 204 can be transparent or translucent. In one or more embodiments, the outer wall 104 of the power unit 100 can be configured to include a window through which the outer tank wall 203 and optionally any liquid 223 present in the tank 201 (or specifically in the reservoir 204) can be visible when the cartridge 200 is engaged with the power unit 100. As seen in the embodiment illustrated in FIG. 1, a window 135 is configured as a cut-out in the outer wall 104 of the power unit 100 that is positioned near the proximal end 108 of the power unit. The window 135 preferably is positioned to provide visual access into the chamber 112 of the power unit 100. As illustrated, the cut-out is substantially oval-shaped; however, it is understood that any shape is encompassed herein. In some embodiments, the window 135 may be configured as a notch extending from the proximal end 108 of the outer wall 104 of the power unit 100 a distance toward the distal end 106 of the power unit. In other embodiments, the window 135 may be configured to not have any open borders and thus may expressly exclude a notch configuration as noted above. In certain embodiments, a window 135 may be expressly excluded from the power unit 100. Moreover, the window 135 may be completely open or the window may have a transparent member (e.g., glass or plastic) positioned in the opening defined by the window or covering the window on one or both of the inner surface and outer surface of the outer wall 104 of the power unit 100. In some embodiments, a viewing window may be defined solely by the cartridge 200. For example, the cartridge 200 may be adapted to or configured to engage with the power unit 100 such that the transparent or translucent inner wall 202 and outer tank wall 203 remain partially or completely outside of the power unit. Thus, the cartridge 200 and the power unit may be engaged such that electrical connections are made but the reservoir 204 remains visible. Thus, the transparent or translucent portions through which the liquid in the reservoir 204 is visible may, in some embodiments, define a window through which the liquid is viewable when the cartridge 200 is engaging the power unit 100.

The aerosol delivery device 10 most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

In use, when a cartridge 200 is inserted into the chamber 112 of the power unit 100 (or otherwise coupled with the power unit), the fit may be such that air is capable of passing between the outer surface of the tank wall 203 and the inner surface of the inner frame 112 of the power unit. Thus, when a user puffs on the mouthpiece 209 air may pass between the outer surface of the tank wall 203 and the inner surface of the inner frame 112, pass through an air entry 220 in the cartridge 200, mingle with formed vapor near the vaporizer 219, pass through the aerosol passage 212, and ultimately pass through the exit portal 215. The passage of air as defined above may be effective to cause pressure drop in the power unit 100 that can be sensed by the sensor 143 through the aperture 115.

An input element may be included with the aerosol delivery device (and may replace or supplement an airflow or pressure sensor). The input may be included to allow a user to control functions of the device and/or for output of information to a user. Any component or combination of components may be utilized as an input for controlling the function of the power unit 100. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference. In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included, choosing the total particulate matter (TPM) provided per puff, choosing a specific heating profile to be implemented, choosing a modifiable resistance to drawn, and the like.

Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator. Likewise, a flow sensor may be replaced with a manual actuator, such as a push button.

Although a variety of input elements may be useful with a device as presently disclosed, it can be desirable to avoid or minimize the presence of any external buttons or other physical input methods that can alter the ergonomics of an aerosol delivery device 10. Simultaneously, however, it can be desirable to provide a user with options for control of various functions of the aerosol delivery device, such as the ability to change the level of power that is delivered to the vaporizer 219 in the cartridge 200 from the battery 116 in the power unit 100. The presently disclosed devices are particularly configured with electrical connections between the cartridge 200 and the power unit 100 that allows for one or more coupling orientations of the cartridge with the power unit while maintaining electrical connectivity for powering of the vaporizer 219 in the cartridge. More particularly, while coupling can be via insertion of the cartridge into a chamber in the power unit in some embodiments, it is understood that the cartridge may be coupleable with the power unit in a variety of manners such that the first interface of the power unit and the second interface of the cartridge are in a mating configuration.

Referring to FIG. 1, the power unit 100 and the cartridge 200 each can be defined in relation to an "X axis" (i.e., a longitudinal axis), a "Y axis" (i.e., a first transverse axis that is transverse to the X axis), and a "Z axis" (i.e., a second transverse axis that is transverse to the X axis and is perpendicular to the Y axis). The power unit and the cartridge may be configured such that the first interface of the power unit and the second interface of the cartridge are coupleable one to another in a plural but finite number of different orientations. For example, in some embodiments, the tank 201 of the cartridge 200 can be sized and shaped to engage the chamber 112 of the power unit 100 in a plural but finite number of different orientations, each orientation having the distal end 207 of the cartridge 200 being inserted into the chamber 112 through the opening 110 in the proximal end 108 of the power unit 100. The number of orientations, for example, can be determined by the shape of the tank 201 and the shape of the chamber 112. Referring to FIGS. 2A and 2B, the distal end 207 of the cartridge 200 is configured for insertion to the proximate end 108 of the power unit 100. The electrical contacts 225 of the cartridge 200 and the electrical connectors 120 of the power unit 100 are both oriented substantially in a straight line along the Y axis of the aerosol delivery device. Since only the two electrical contacts 225 and the two electrical connectors 120 are required for heating, the cartridge 200 can be inserted into the chamber 112 of the power unit 100 in either to two possible directions along the Y axis. In other words, the cartridge 200 may be inserted into the chamber 112 in a first orientation or in a second orientation rotated 180° around the X axis and achieve the same result for heating of the device. In such embodiments, operation of the aerosol delivery device proceeds under the same conditions regardless of cartridge orientation.

Although the figures illustrate embodiments wherein a portion of the cartridge 200 is inserted into a portion of the power unit 100, it is understood that this is for illustration purposes only, and the disclosure encompasses further modes of interconnection of the power unit and the cartridge such that the first interface and the second interface, respectively, are coupleable. For example, in some embodiments, the cartridge may comprise a receptacle such that a portion of the power unit is inserted into a portion of the cartridge. Likewise, the cartridge 200 and the power unit 100 may interconnect through a surface-to-surface connection such electrical engagements are made but one portion of the cartridge or power unit does not necessarily "insert" into a receptacle in the other of the cartridge and the power unit. Thus, the present disclosure is intended to provide embodiments for establishing electrical connections between a cartridge and a power unit without express limitation to the mechanical connection of the two elements. As such, the cartridge and the power unit can be defined in relation to being coupleable one to another, which coupling may include a mechanical interconnection as described herein or other types of mechanical interconnections.

In one or more embodiments according to the present disclosure, cartridge orientation can be utilized as a selector for setting at least one operational profile of an aerosol delivery device. As used herein, an operational profile is intended to refer to any mode of operation of the aerosol delivery device that may be subject to a plurality of variations. For example, operational profiles can relate to power delivery from the battery 116 of the power unit 100 to the vaporizer 219 of the cartridge 200. In one operational profile, a "high power" mode can be selected and a "low power" mode can be selected whereby the controller can be configured to cause the battery 116 in the power unit 100 to deliver more electrical energy to the vaporizer 219 in the cartridge when in the high power mode that when in the low power mode, and the controller can be configured to cause the battery to deliver less electrical energy to the vaporizer when in the low power mode that when in the high power mode. The selected operational profile (i.e., high power mode or low power mode under this specific example embodiment offering selectable high power and low power modes) can thus affect the amount of aerosol that is produced during draw on the device (i.e., more aerosol being produced in a high power mode than in a low power mode and less aerosol being produced in a low power mode than in a high power mode). The relative amount of current delivered in the high power mode and the low power mode can vary so long as there is an actual difference in current delivered in the different modes. For example, in some embodiments, the control components may be provided with at least two defined and fixed power levels with a first fixed power level being greater than a second fixed power level or a first fixed power level being less than a second fixed power level. Further, one of the power levels may be a fixed power level and the other power level may be a variable power level. The relative differences between a "high" power level and a "low" power level may be quantifiable based upon one or more measurable characteristics of use of the device. For example, operating at a first power level (e.g., a "high" power level) may be effective to provide a first total particulate matter (TPM) level while operating at a second power level (e.g., a "low" power level) may be effective to provide a second TPM level that is less than the first TPM level by at least 5%, at least 10%, at least 20%, at least 30%, at least 40%, or at least 50% (e.g., about 5% to about 90%, about 10% to about 80%, or about 15% to about 75% less) based on the total TPM delivered in puffs of the same duration. In addition to the foregoing, the "high" and "low" power levels may be adjustable based on one or more further characteristics of the device. For example, the respective power levels may be adjusted based upon the battery voltage level at a given time. Likewise, the power levels may be adjustable to take into consideration the actual vaporizer that is utilized in the device understanding that a first vaporizer may be adapted to or configured to provide greater aerosol formation and a second vaporizer of a different structure.

While the foregoing provides a detailed discussion of how cartridge orientation may be utilized for adjusting a power level, it is understood that the same principle may be applied to any number of other controllable functions of the device. For example, cartridge orientation may control an overall status of the device such that a first orientation may be adapted to or configured to cause the device to be in an "on" or functional mode and a second orientation of the cartridge may be adapted to or configured to cause the device to be in an "off" or non-functional mode. In some embodiments, a first orientation of the cartridge may be adapted to or configured to enable wireless communication capabilities of the device while a second orientation may be adapted to configured to disable wireless communication capabilities. In some embodiments, a first orientation of the cartridge may be adapted to or configured to cause a first visual effect (e.g., LED color or lighting pattern) while a second orientation may be adapted to configured to cause a second, different visual effect. In some embodiments, a first orientation of the cartridge may be adapted to or configured to enable haptic effects of the device while a second orientation may be adapted to configured to disable such haptic effects or enable different haptic effects. In some embodiments, a first orientation of the cartridge may be adapted to or configured to enable a first set of user settings of the device while a second orientation may be adapted to configured to enable a second, different set of user settings of the device.

In some embodiments, the cartridge is rotatable about the longitudinal axis of the cartridge housing so as to be coupleable with the power unit in at least a first orientation relative to the power unit and a second, different orientation relative to the power unit. A further described herein, the cartridge and the power unit can be configured to allow for any variety of different orientations based upon the rotation of the cartridge about the longitudinal axis.

As further discussed below, the power unit can comprise processing circuitry, and such processing circuitry can be configured for detecting whether the cartridge is present in the chamber in the first orientation or the second, different orientation (or even further, different orientations). Further, the processing circuitry can be configured for executing a control function assigned to the respective orientation of the cartridge relative to the power unit when the cartridge is coupled with the power unit. Example embodiments of structural configurations whereby cartridge orientations can be distinguished from each other are described below. Such example embodiments are illustrative in nature and should not be viewed as limiting the scope of the present disclosure.

In some embodiments, the present disclosure provides for varied operation of the aerosol delivery device based upon the orientation of the cartridge 200 relative to the power unit 100 by utilizing three electrical contacts in the cartridge and three corresponding electrical contacts in the power unit. Example embodiments are illustrated in FIG. 3A and FIG. 3B wherein it is understood that only relevant portions of the cartridge 200 and the power unit 100 are illustrated, and the cartridge and/or the power unit may include any further elements as disclosed herein or as otherwise would be expected to be useful in a cartridge and/or power unit useful in forming an aerosol delivery device.

As seen in FIG. 3A, the distal end 207 of the cartridge 200 again includes two electrical contacts 225a and 225b; however, the cartridge further includes a third electrical contact 240 that functions as an orientation identifier. Electrical contact 225a is electrically connected to the vaporizer 219 via electrical line 251, and electrical contact 225b is electrically connected to the vaporizer via electrical line 252. Electrical contact 240 is electrically connected to electrical line 251 via electrical line 253. As before, electrical contacts 225a and 225b must be in electrical contact with the battery 116 in the power unit 100 for power delivery to proceed to the vaporizer 219. The electrical contact 240 however, can be used to identify cartridge orientation based upon whether or not electrical contact 240 makes an electrical connection with the power unit 100. As seen in FIG. 3A, the power unit 100 includes electrical connectors 120a and 120b, which are configured for electrical connection with either of electrical contacts 225a and 225b in the cartridge 200. As illustrated in FIG. 3A, the cartridge 200 is oriented so that electrical contact 225a will make an electrical connection with electrical connector 120a, electrical contact 225b will make an electrical connection with electrical connector 120b, and electrical contact 240 will make an electrical connection with a third electrical connector 160. In FIG. 3B, the cartridge 200 has been rotated 180° around the X axis of the cartridge relative to the orientation illustrated in FIG. 3A. Accordingly, as shown in FIG. 3B, the cartridge 200 is oriented so that electrical contact 225a will make an electrical connection with electrical connector 120b, electrical contact 225b will make an electrical connection with electrical connector 120a, and electrical contact 240 will not make an electrical connection with the third electrical connector 160. As such, the electrical connections between the cartridge 200 and the power unit 100 are now different based upon which orientation is utilized.

The controller in the power unit 100 can be configured to operate under a defined profile based upon the orientation of the cartridge 200—i.e., when oriented for an electrical connection between electrical contact 240 and electrical connector 160 as shown in FIG. 3A or when oriented for no electrical connection between electrical contact 240 and electrical connector 160 as shown in FIG. 3B. For example, in some embodiments, a first operational profile can be a default profile, and a second operational profile can be an activated profile. The controller can be configured to implement the default profile when electrical contacts 225a and 225b are in electrical connection with electrical connectors 120a and 120b but when there is not an electrical connection with electrical connector 160, and the controller can be configured to implement the activated profile when electrical contacts 225a and 225b are in electrical connection with electrical connectors 120a and 120b and when there is an electrical connection with electrical connector 160 (e.g., the electrical connection between electrical contact 240 and electrical connector 160 discussed above). Alternatively, the default profile and the activated profile may be reversed. The power unit 100 can include a single driver unit to control operation of the vaporizer 219 in the cartridge 200 since the same two electrical connectors (120a and 120b) and the same two electrical connectors (225a and 225b) are utilized in these embodiments to power the vaporizer while the third electrical connector 240 and the third electrical connector 160 are only used to identify cartridge orientation. Any suitable function can be utilized by the controller to determine in which orientation the cartridge is positioned. For example, the controller may be adapted to or configured to execute a test routine each time the cartridge is coupled to the power unit and/or each time a user attempts to activate the vaporizer. Such test routine may include delivering a test current through electrical contact 240 to determine whether a completed electrical circuit is achieved and/or to check for a specific resistance load.

In some embodiments, the present disclosure provides for varied operation of the aerosol delivery device based upon the orientation of the cartridge 200 relative to the power unit 100 by utilizing two electrical contacts in the cartridge and four electrical contacts in the power unit. Example embodiments are illustrated in FIG. 4A and FIG. 4B wherein it is understood that only relevant portions of the cartridge 200 and the power unit 100 are illustrated, and the cartridge and/or the power unit may include any further elements as disclosed herein or as otherwise would be expected to be useful in a cartridge and/or power unit useful in forming an aerosol delivery device.

As seen in FIG. 4A, the distal end 207 of the cartridge 200 again includes two electrical contacts 225a and 225b; however, rather than being aligned along the Y axis of the cartridge, the two electrical contacts are positioned at right angles relative to each other. Electrical contact 225a is electrically connected to the vaporizer 219 via electrical line 251, and electrical contact 225b is electrically connected to the vaporizer via electrical line 252. The power unit 100 includes four electrical connectors—120a, 120b, 120c, and 120d, and the electrical connectors are configured such that only two of the electrical connectors will form an electrical connection with the two electrical contacts 225b and 225b of the cartridge 200 based on a given cartridge orientation. As illustrated in FIG. 4A, the cartridge 200 is oriented so that electrical contact 225a will make an electrical connection with electrical connector 120a, and electrical contact 225b will make an electrical connection with electrical connector 120b. Electrical connectors 120c and 120d make no electrical connections in this orientation. In FIG. 4B, the cartridge 200 has been rotated 180° around the X axis of the cartridge relative to the orientation illustrated in FIG. 4A. Accordingly, as shown in FIG. 4B, the cartridge 200 is oriented so that electrical contact 225a will make an electrical connection with electrical connector 120c, and electrical contact 225b will make an electrical connection with electrical connector 120d. Electrical connectors 120a and 120b make no electrical connections in this orientation.

According to such embodiments, the controller of the power unit can be configured to check for an electrical connection at electrical connectors 120a and 120b and separately check for an electrical connection at electrical connectors 120c and 120d. As only one of the pairs of electrical connectors (pair 1, consisting of connectors 120a and 120b or pair 2, consisting of connectors 120c and 120d) will exhibit an electrical resistance depending upon the cartridge orientation, the controller can be configured to operate under a defined profile based upon which set of electrical connectors registers a resistance. To determine the given orientation, for example, the controller may be adapted to configured to apply a current to the connection(s) and determine whether a resistance is detected, the presence or absence of the resistance being an indicator of the presence or absence of a given orientation. The delivered current may be of a magnitude that is sufficient to enable the evaluation of the orientation without actually activating the vaporizer. In further embodiments, cartridge orientation detection may be combined with or run in parallel with a cartridge authentication routine. For example, instead of only evaluating for the presence or absence of a resistance across pairs of electrical connections, each electrical connection may have a defined resistance value or an acceptable resistance range, and the detection routine from the controller may be adapted to or configured to confirm that a measured resistance across a pair of electrical contacts meets the defined resistance or is within the acceptable resistance range. Still further, an electrical property may be utilized in this manner to identify a characteristic of the consumable liquid present in the cartridge. For example, the resistance value or resistance range across a pair of electrical contacts may correspond to a specified flavor, strength of an active agent (e.g., nicotine) present in the liquid, or other characteristic, and the controller may be adapted to or configured to execute a defined operating profile that corresponds to the identified characteristic of the liquid in the cartridge. Electrical circuit designs suitable for carrying out such embodiments of the present disclosure are described in U.S. Pat. No. 10,031,183 to Novak, III, et al. and U.S. Pat. Pub. No. 2015/0257445 to Henry, Jr., et al., the disclosures of which are incorporated herein by reference.

From the foregoing, it thus can be seen that the controller can be configured to implement a first profile when electrical connectors 120a and 120b register a resistance, and the controller can be configured to implement a second profile when electrical connectors 120c and 120d register a resistance. In one or more embodiments, two separate driver circuits can be included in the power unit 200 in order to control flow of power to the vaporizer 219 in the cartridge 200 through the two separate pairs of electrical connectors.

In some embodiments, the present disclosure provides for varied operation of the aerosol delivery device based upon the orientation of the cartridge 200 relative to the power unit 100 by utilizing two electrical contacts in the cartridge and three electrical contacts in the power unit. Example embodiments are illustrated in FIG. 5A and FIG. 5B wherein it is understood that only relevant portions of the cartridge 200 and the power unit 100 are illustrated, and the cartridge and/or the power unit may include any further elements as disclosed herein or as otherwise would be expected to be useful in a cartridge and/or power unit useful in forming an aerosol delivery device.

As seen in FIG. 5A, the distal end 207 of the cartridge 200 includes two electrical contacts 225a and 225b that are substantially aligned along the Y axis of the cartridge. One of the electrical contacts (electrical contact 225b, as illustrated in FIG. 5A and FIG. 5B) is positioned substantially in the geometric center of the distal end 207 of the cartridge 200 so that it can make an electrical connection with an electrical connector in the power unit 200 regardless of the orientation of the cartridge. Electrical contact 225a is electrically connected to the vaporizer 219 via electrical line 251, and electrical contact 225b is electrically connected to the vaporizer via electrical line 252. The power unit 100 includes three electrical connectors—120a, 120b, and 120c, and the electrical connectors are configured such that only two of the electrical connectors will form an electrical connection with the two electrical contacts 225b and 225b of the cartridge 200 based on a given cartridge orientation. As illustrated in FIG. 5A, the cartridge 200 is oriented so that electrical contact 225a will make an electrical connection with electrical connector 120a, and electrical contact 225b will make an electrical connection with electrical connector 120b. Electrical connector 120c makes no electrical connection in this orientation. In FIG. 5B, the cartridge 200 has been rotated 180° around the X axis of the cartridge relative to the orientation illustrated in FIG. 5A. Accordingly, as shown in FIG. 5B, the cartridge 200 is oriented so that electrical contact 225a will make an electrical connection with electrical connector 120c, and electrical contact 225b will still make an electrical connection with electrical connector 120b. Electrical connector 120a makes no electrical connection in this orientation.

According to such embodiments, the controller of the power unit can be configured to check for an electrical connection at electrical connectors 120a and 120b and separately check for an electrical connection at electrical connectors 120b and 120c. As only one of the pairs of electrical connectors (pair 1, consisting of connectors 120a and 120b or pair 2, consisting of connectors 120b and 120c) will exhibit an electrical resistance depending upon the cartridge orientation, the controller can be configured to operate under a defined profile based upon which set of electrical connectors registers a resistance. Thus, the controller can be configured to implement a first profile when electrical connectors 120a and 120b register a resistance, and the controller can be configured to implement a second profile when electrical connectors 120b and 120c register a resistance. In one or more embodiments, two separate driver circuits can be included in the power unit 200 in order to control flow of power to the vaporizer 219 in the cartridge 200 through the two, unique pairings of electrical connectors. Moreover, means for detecting a given cartridge orientation can include any method as otherwise described herein.

In some embodiments, the present disclosure provides for varied operation of the aerosol delivery device based upon the orientation of the cartridge 200 relative to the power unit 100 by utilizing one or more added sensor elements in addition to the two electrical contacts in the cartridge and two electrical contacts in the power unit utilized to power the vaporizer 219 in the cartridge. Example embodiments are illustrated in FIG. 6A and FIG. 6B wherein it is understood that only relevant portions of the cartridge 200 and the power unit 100 are illustrated, and the cartridge and/or the power unit may include any further elements as disclosed herein or as otherwise would be expected to be useful in a cartridge and/or power unit useful in forming an aerosol delivery device.

As seen in FIG. 6A, the distal end 207 of the cartridge 200 includes two electrical contacts 225a and 225b that are substantially aligned along the Y axis of the cartridge. Electrical contact 225a is electrically connected to the vaporizer 219 via electrical line 251, and electrical contact 225b is electrically connected to the vaporizer via electrical line 252. The power unit 100 includes two electrical connectors 120a and 120b that are substantially aligned along the Y axis of the power unit and that are configured to form an electrical connection with the two electrical contacts 225b and 225b of the cartridge 200 regardless of the cartridge orientation. As illustrated in FIG. 6A, the cartridge 200 is oriented so that electrical contact 225a will make an electrical connection with electrical connector 120a, and electrical contact 225b will make an electrical connection with electrical connector 120b. In FIG. 6B, the cartridge 200 has been rotated 180° around the X axis of the cartridge relative to the orientation illustrated in FIG. 6A. Accordingly, as shown in FIG. 6B, the cartridge 200 is oriented so that electrical contact 225a will make an electrical connection with electrical connector 120b, and electrical contact 225b will make an electrical connection with electrical connector 120a. In addition to the electrical contacts 225a and 225b, the cartridge 200 includes a magnetic connector 230a positioned similarly to the mating connector 203 illustrated in FIG. 1. In the embodiments of FIG. 6A and FIG. 6B, the connector 230a is a magnet, and a corresponding metal plate 121a is present in the power unit 100. The metal plate can be any material that is adapted for forming a magnetic connection with the magnetic connector 230a. In addition to the metal plate 121a, a Hall effect sensor 155 is positioned proximate the metal plate. The Hall effect sensor can be present surrounding the metal plate 121a or otherwise sufficiently close to the metal plate to activate when the magnetic connector 230a forms a magnetic connection with the metal plate. One example of a suitable Hall effect current sensor is the MLX91205 IMC-Hall® Current Sensor from Melexis NV of Ieper, Belgium. Incorporation of Hall effect sensors in aerosol delivery devices is described in U.S. Pub. No. 2017/0196263 to Sur, the disclosure of which is incorporated herein by reference. As illustrated in FIG. 6A, the cartridge 200 is oriented so that the magnetic connector 230a will contact or be in sufficiently close proximity to the metal plate 121a to activate the Hall sensor 155. In FIG. 6B, the cartridge 200 is oriented so that the magnetic connector 230a will not contact or be in sufficiently close proximity to the metal plate 121a to activate the Hall sensor 155. In some embodiments, the Hall effect sensor may be adapted to or configured to detect the field in the absence of the metal plate 121a, which expressly may be omitted.

According to such embodiments, the controller of the power unit can be configured to check for an electrical connection at electrical connectors 120a and 120b and separately check for activation of the Hall sensor 155. Thus, the controller can be configured to implement a first profile when electrical connectors 120a and 120b register a resistance and the Hall sensor 155 is activated, and the controller can be configured to implement a second profile when electrical connectors 120a and 120n register a resistance but the Hall sensor is not activated. The presence of the Hall effect sensor may further be useful cartridge authentication and/or identifying a specific property of the cartridge and/or a liquid therein that may provide direction to the controller in relation a desired control profile to be implemented. For example, the Hall effect sensor may be adapted to or configured to determine a magnetic field magnitude, and different cartridges may be configured (e.g., with different sized magnets providing different field strengths) so that the Hall effect sensor can identify a cartridge characteristic associated with a given cartridge configuration.

In some embodiments, instead of utilizing a Hall effect sensor, an electromagnetic sensor 122a may be present and may be adapted to or configured to read a defined electromagnetic signal. For example, a light sensor 122a may be adapted to or configured to identify a color of a color label 232a present on the cartridge. The presence of the color signal (as would be achieved in FIG. 6C) or the absence of the color signal (as would be achieved in FIG. 6D) may be used to identify a specific cartridge orientation and thus a defined operation parameter. Similarly, the color signal may be variable between different cartridges, and the electromagnetic sensor 122a may be adapted to or configured identify the specific color and implement a specific operation based upon the identified color.

The foregoing are example embodiments of the present disclosure and should not be viewed as limiting the types of elements that can be utilized to identify cartridge orientation and thus allow for implementation of multiple different operational profiles based upon the identified orientation. As further examples, optical sensors, infrared sensors, mechanical switches, or the like further may be utilized to differentiate between two or more different orientations of the cartridge 200 in the chamber 112 of the power unit 100. Likewise, it is not required for the differentiating element(s) to be present at the distal end 207 of the cartridge or at a bottom wall of the chamber 112 of the power unit 100. For example, switches, sensors, contacts, or the like may be present at any position along the outer tank wall 203 and at any position on the side wall 114b of the inner frame 114 of the power unit 100.

In some embodiments, the present disclosure further can be directed to methods for selecting an operational profile of an aerosol delivery device. The methods in particular can be carried out by one or more components that may be implemented on the PCB 141 in the power unit 100 in the power unit in combination with a user-selected orientation of the cartridge 200 relative to the power unit. For example, the PCB may include processing circuitry that can be configured to perform data processing, application execution, and/or other processing and management services. The processing circuitry may be implemented via one or more integrated circuits, which may each include one or more chips. The processing circuitry and/or one or more further components of the aerosol delivery device may therefore, in some embodiments, be configured to implement an embodiment of a system on a chip. In some example embodiments, the processing circuitry may include a processor and may further include memory. The processing circuitry may be in communication with or otherwise control vaporizer circuitry that can be present in the cartridge 200 as well as further components that may be present in the aerosol delivery devices, such as the light source 139, haptic components, charging components, and the like.

The processor may be embodied in a variety of forms. For example, the processor may be embodied as various hardware processing means, such as a microprocessor, a coprocessor, a controller or various other computing or processing devices including integrated circuits such as, for example, an ASIC (application specific integrated circuit), an FPGA (field programmable gate array), some combination thereof, or the like. Moreover, the processor may comprise a plurality of processors. The plurality of processors may be in operative communication with each other and may be collectively configured to perform one or more functionalities. In some example embodiments, the processor may be configured to execute instructions that may be stored in the memory and/or that may be otherwise accessible to the processor. As such, whether configured by hardware or by a combination of hardware and software, the processor may be capable of performing operations according to various embodiments while being configured accordingly.

In some example embodiments, the memory may include one or more memory devices. Memory may include fixed and/or removable memory devices. In some embodiments, the memory may provide a non-transitory computer-readable storage medium that may store computer program instructions that may be executed by the processor. In this regard, the memory may be configured to store information, data, applications, instructions and/or the like for enabling the aerosol delivery device to carry out various functions in accordance with one or more example embodiments. In some embodiments, the memory may be configured to store information, data, applications, instructions and/or the like related to one or more control profiles that may be executed by the processing circuitry based upon a given orientation of a cartridge relative to the power unit.

In some example embodiments, the aerosol delivery device may include vaporizer circuitry. The vaporizer circuitry may be at least partially embodied as various means, such as circuitry, hardware, a computer program product comprising computer readable medium (for example, the memory) storing computer readable program instructions executable by a processing device (for example, the processor), or some combination thereof. In some embodiments, the processor (or the processing circuitry) may include, or otherwise control, the vaporizer circuitry. The vaporizer circuitry may be configured to operatively engage a heating element (e.g., heating element 219) via one or more electrical connections (e.g., electrical connectors 121), the heating element being implemented in a cartridge (e.g., cartridge 200). For example, the vaporizer circuitry may be configured to operatively engage the electrical connectors 121 to supply electrical current to the heating element 219 via electrical contacts 230 in accordance with some example embodiments. The vaporizer circuitry may accordingly be configured to control the supply of power to a heating element (e.g., heating element 219) for heat generation.

Methods for selecting a control profile for an aerosol delivery device can comprise providing a power unit 100 and a cartridge 200 according to embodiments encompassed by the present disclosure wherein the cartridge can be configured to engage the power unit in a plurality of different orientations to form a functioning aerosol delivery device, each of the plurality of different orientations being effective to cause operation of the aerosol delivery device according to a different control profile. The methods thus can include a step of coupling or combining a cartridge with a power unit in one of the plurality of orientations. In example embodiments, coupling or combining may include inserting the cartridge into a chamber of the power unit. The methods further may be defined solely in relation to the operational aspects of the device. For example, the methods can comprise the processing circuitry carrying out an orientation routine wherein the processing circuitry checks for a signal indicative of a specific orientation of the cartridge relative to the power unit. Referencing FIG. 3A and FIG. 3B, in example embodiments, the processing circuitry can check for the presence of an electrical connection between electrical contact 240 and electrical connector 160. As discussed above, the presence of the electrical connection between electrical contact 240 and electrical connector 160 can be indicative of a first orientation of the cartridge, and the absence of the electrical connection between electrical contact 240 and electrical connector 160 can be indicative of a second orientation of the cartridge. Referencing FIG. 4A and FIG. 4B, in example embodiments, the processing circuitry can check for the presence of an electrical connection between the electrical contacts 225a and 225b and either the first pair of electrical connectors (i.e., electrical connectors 120a and 120b) or the second pair of electrical connectors (i.e., electrical connectors 120c and 120d). As discussed above, the presence of the electrical connection between electrical contacts 225a and 225b and the first pair of electrical connectors can be indicative of a first orientation of the cartridge, and the presence of the electrical connection between electrical contacts 225a and 225b and the second pair of electrical connectors can be indicative of a second orientation of the cartridge. Referencing FIG. 5A and FIG. 5B, in example embodiments, the processing circuitry can check for the presence of an electrical connection between the electrical contacts 225a and 225b and either the first pair of electrical connectors (i.e., electrical connectors 120a and 120b) or the second pair of electrical connectors (i.e., electrical connectors 120b and 120c). As discussed above, the presence of the electrical connection between electrical contacts 225a and 225b and the first pair of electrical connectors can be indicative of a first orientation of the cartridge, and the presence of the electrical connection between electrical contacts 225a and 225b and the second pair of electrical connectors can be indicative of a second orientation of the cartridge. Referencing FIG. 6a and FIG. 6B, in example embodiments, the processing circuitry can check for the presence of a signal from a sensor, such as a Hall effect sensor. As discussed above, the presence of the signal from the sensor (e.g., the Hall effect sensor) can be indicative of a first orientation of the cartridge, and the absence of the signal from the sensor can be indicative of a second orientation of the cartridge. The processing circuitry also can be configured to select and/or execute a defined control profile based upon the identified cartridge orientation.

A control profile to be selected and/or executed by the processing circuitry can comprise a single function (e.g., implementing a defined level of power delivery from the battery to the vaporizer) or can comprise a plurality of functions that are combined to provide a specific operational effect. In example embodiments, a power unit 100 and an associate cartridge 200 can be configured to engage in only two alternate orientations. The present disclosure, however, envisions a wide variety of possible alternative orientations that can be achieved by altering the shape of the cartridge 100 and the chamber 212 of the power unit. For example, a cartridge with an equilateral triangular cross-section may be inserted into a chamber with the same cross-section in three different orientations. Appropriate electrical connections and/or sensor elements may then be included so that each of the three different orientations may correspond to a different control profile to be executed by the processing circuitry. As such, in example embodiments, the present disclosure encompasses aerosol delivery devices wherein the cartridge may engage the control unit in at least two, at least three, or at least four different orientations, such as two to eight, two to six, or two to five different orientations. It will be appreciated that such alternative embodiments can be provided with an appropriate number of connectors/contacts/Hall effect sensors and arrangements thereof to facilitate detection.

Example embodiments of methods according to the present disclosure are illustrated in reference to FIG. 7, which shows a process flow for selecting a control profile from a total of two possible different control profiles. In FIG. 7, the process can comprise checking for a cartridge orientation at step 701. Such step can comprise, for example, the processing circuitry causing a low power pulse to be delivered to the electrical connectors in the power unit to check for an electrical resistance across the electrical connectors. The process further can comprise identifying a current cartridge orientation status at step 703. Such step can comprise, for example, the process circuitry recognizing a signal that is indicative of the cartridge orientation, such as recognizing a current resistance across a first defined pair of electrical connectors or across a second defined pair of electrical connectors (e.g., referencing the example embodiments of FIG. 4A and FIG. 4B or FIG. 5A and FIG. 5B), or such as recognizing a signal received from a sensor (e.g., referencing the example embodiments of FIG. 6A and FIG. 6B). The process additionally can comprise implementing a control profile assigned to the identified cartridge orientation status at step 705. Such step can comprise executing a defined control profile that can be provided with the control circuitry via hardware, software, or any combination thereof. For example, the memory of the control circuit may include a lookup table including operating parameters correlated to each specific control profile, and the implementing step 705 can include retrieving the operating parameters from the memory and executing the operating parameters. As a further, non-limiting example, the different control profiles may be hardwired into the control circuitry such that establishment of an electrical connection utilizing a first defined set of electrical connectors in the power unit will cause the processing circuitry to execute the operating parameters associated with a first control profile while establishment of an electrical connection utilizing a second defined set of electrical connectors in the power unit will cause the processing circuitry to execute the operating parameters associated with a second control profile.

In one or more embodiments, the aerosol delivery device can be configured for connection with a power source via the external connection element 118. The aerosol delivery device thus can be configured for recharging via connection with any suitable adaptor, such as a Universal Serial Bus (USB) connector, suitable for connecting the power unit with a suitable power source. For example, an adaptor including a USB connector at one end and a power unit connector at an opposing end is disclosed in U.S. Pat. Pub. No. 2014/0261495 to Novak et al., which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine). In some embodiments, an aerosol precursor composition may comprise nicotine in a free-base form and/or a protonated form. Protonation may be achieved through inclusion of one or more acids in the aerosol precursor composition. For example, organic acids, such as levulinic acid, succinic acid, lactic acid, and pyruvic acid, may be included in the aerosol precursor with nicotine in amounts up to being equimolar (based on total organic acid content) with the nicotine. Any combination of organic acids can be used. For example, the aerosol precursor can include about 0.1 to about 0.5 moles of any one or more of the above-noted organic acids per one mole of nicotine, up to a concentration wherein the total amount of organic acid present is equimolar to the total amount of nicotine present in the aerosol precursor composition.

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference. Other aerosol precursors that may be employed include the aerosol precursors that have been incorporated in the VUSE® product by R. J. Reynolds Vapor Company, the BLU' product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 1 ml or more, about 2 ml or more, about 5 ml or more, or about 10 ml or more of the aerosol precursor composition may be included.

The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

As noted above, in some embodiments the aerosol precursor composition comprises a glycerol-based liquid. In other embodiments, however, the aerosol precursor composition may be a water-based liquid. In such embodiments, the water-based aerosol precursor composition may be comprised of more than approximately 60% water. For example, in some embodiments about 60% or greater water by weight, or about 65% or greater water by weight, or about 70% or greater water by weight, or about 75% or greater water by weight, or about 80% or greater water by weight, or about 85% or greater water by weight, or about 90% or greater water by weight, based on the total weight of the water-based aerosol precursor composition. In some embodiments, the water-based liquid may include up to approximately 10% propylene glycol. For example, in some embodiments the percentage of propylene glycol in the water-based liquid may be in the inclusive range of approximately 4% to approximately 5%. In some embodiments, the water-based liquid may include up to approximately 10% flavorant. For example, in some embodiments the percentage of flavorant(s) of the water-based liquid may be in the inclusive range of approximately 3% to approximately 7%. In some implementations, the water-based liquid may include up to approximately 1% nicotine. For example, in some embodiments the percentage nicotine in the water-based liquid may be in the inclusive range of approximately 0.1% to approximately 0.3%. In some embodiments, the water-based liquid may include up to approximately 10% cyclodextrin. For example, in some embodiments the percentage cyclodextrin in the water-based liquid may be in the inclusive range of approximately 3% to 5%. In still other embodiments, the aerosol precursor composition may be a combination of a glycerol-based liquid and a water-based liquid. For example, some embodiments may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled *Aerosolisable Formulation*; GB 1817864.0, filed Nov. 1, 2018, titled *Aerosolisable Formulation*; GB 1817867.3, filed Nov. 1, 2018, titled *Aerosolisable Formulation*; GB 1817865.7, filed Nov. 1, 2018, titled *Aerosolisable Formulation*; GB 1817859.0, filed Nov. 1, 2018, titled *Aerosolisable Formulation*; GB 1817866.5, filed Nov. 1, 2018, titled *Aerosolisable Formulation*; GB 1817861.6, filed Nov. 1, 2018, titled *Gel and Crystalline Powder*; GB 1817862.4, filed Nov. 1, 2018, titled *Aerosolisable Formulation*; GB 1817868.1, filed Nov. 1, 2018, titled *Aerosolised Formulation*; and GB 1817860.8, filed Nov. 1, 2018, titled *Aerosolised Formulation*, each of which is incorporated by reference herein in its entirety.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
a power unit comprising:
 a power unit housing having a distal end, a proximal end, and a longitudinal axis extending between the distal end and the proximal end;
 a power source positioned within the power unit housing;
 a first interface defined at the proximal end of the power unit housing; and
 processing circuitry; and
a cartridge that is coupleable with the power unit, the cartridge comprising:
 a cartridge housing having a distal end defining a second interface, a proximal end, and a longitudinal axis extending between the distal end and the proximal end, the cartridge housing being configured for containing an aerosol precursor composition; and
 a vaporizer positioned within the cartridge housing and operable to vaporize the aerosol precursor composition;
wherein the cartridge is configured for rotation about the longitudinal axis of the cartridge housing so as to be coupleable with the power unit in at least a first orientation relative to the power unit and a second, different orientation relative to the power unit; and
wherein the processing circuitry of the power unit is configured for detection of whether the cartridge is present in the first orientation or the second, different orientation and executing a control function assigned to the respective orientation.

2. The aerosol delivery device of claim 1, wherein the power unit further comprises two electrical connectors positioned at the first interface of the power unit housing, and wherein the cartridge further comprises two electrical contacts positioned in or on the cartridge housing and configured for making an electrical connection with the two electrical connectors of the power unit when the cartridge is coupled with the power unit, the electrical connection being configured for delivery of electrical current from the power source in the power unit to the vaporizer in the cartridge.

3. The aerosol delivery device of claim 2, wherein the power unit comprises a first electrical connector, a second electrical connector, and a third electrical connector.

4. The aerosol delivery device of claim 3, wherein:
the cartridge comprises a first electrical contact, a second electrical contact, and a third electrical contact;
the first electrical contact and the second electrical contact are in electrical connection with the first electrical connector and the second electrical connector in each of the first orientation and the second, different orientation of the cartridge; and
the third electrical contact is in electrical connection with the third electrical connector in only one of the first orientation and the second, different orientation of the cartridge.

5. The aerosol delivery device of claim 3, wherein:
the cartridge comprises a first electrical contact and a second electrical contact;
the first electrical contact and the second electrical contact are in electrical connection with the first electrical connector and the second electrical connector in the first orientation of the cartridge; and
the first electrical contact and the second electrical contact are in electrical connection with the second electrical connector and the third electrical connector in the second, different orientation of the cartridge.

6. The aerosol delivery device of claim 2, wherein power unit comprises a first set of two electrical connectors and a second set of two electrical connectors.

7. The aerosol delivery device of claim 6, wherein:
the two electrical contacts of the cartridge are in electrical connection with the first set of electrical connectors in the first orientation of the cartridge; and
the two electrical contacts of the cartridge are in electrical connection with the second set of electrical connectors in the second, different orientation of the cartridge.

8. The aerosol delivery device of claim 2, wherein the power unit comprises a sensing element configured for providing a signal dependent upon whether the cartridge is in the first orientation or the second, different orientation, said signal being detectable by the processing circuitry.

9. The aerosol delivery device of claim 8, wherein the sensing element comprises a Hall effect sensor.

10. The aerosol delivery device of claim 1, wherein the control function includes a power delivery profile.

11. The aerosol delivery device of claim 10, wherein the processing circuitry is configured for directing delivery of electrical current from the power source in the power unit to the vaporizer in the cartridge according to a first power delivery profile when the cartridge is in the first orientation and is configured for directing delivery of electrical current from the power source in the power unit to the vaporizer in the cartridge according to a second, different power delivery profile when the cartridge is in the second, different orientation.

12. The aerosol delivery device of claim 1, wherein the control function includes powering the aerosol delivery device on and off.

13. The aerosol delivery device of claim 1, wherein the control function includes enabling or disabling a wireless communication capability of the aerosol delivery device.

14. The aerosol delivery device of claim 1, wherein the control function includes activating a visual effect or a haptic effect of the aerosol delivery device.

15. The aerosol delivery device of claim 1, wherein the control function includes enabling a set of user settings of the device.

* * * * *